United States Patent [19]
Aalto et al.

[11] Patent Number: 4,597,758
[45] Date of Patent: Jul. 1, 1986

[54] SEALING CLOSURE FOR A LUER FITTING IN OPEN COMMUNICATION WITH A PRESSURIZED LIQUID SUPPLY

[75] Inventors: William R. Aalto, Spring Grove; Rick R. Ruschke, McHenry, both of Ill.

[73] Assignee: Baxter Travenol Laboratories, Inc., Deerfield, Ill.

[21] Appl. No.: 420,981

[22] Filed: Sep. 21, 1982

[51] Int. Cl.⁴ ............................................. A61M 5/005
[52] U.S. Cl. ...................................... 604/256; 604/263
[58] Field of Search ................. 604/93, 192, 194, 256, 604/263, 283, 407, 905, 124, 179, 415; 215/341, 347; 285/332

[56] References Cited

U.S. PATENT DOCUMENTS

| | | | |
|---|---|---|---|
| 2,687,731 | 8/1954 | Iarussi et al. | 604/256 |
| 3,307,552 | 3/1967 | Strawn | 604/256 |
| 4,085,737 | 4/1978 | Bordow | 604/263 |
| 4,124,025 | 11/1978 | Alrazi | 604/192 |
| 4,248,246 | 2/1981 | Ikeda | 604/263 |
| 4,266,815 | 5/1981 | Cross | 285/332 |
| 4,296,949 | 10/1981 | Muetterties et al. | 604/905 |
| 4,318,400 | 3/1982 | Peery et al. | |
| 4,417,887 | 11/1983 | Koshi | 604/192 |
| 4,445,896 | 5/1984 | Gianturco | 604/283 |
| 4,452,473 | 6/1984 | Ruschke | 285/81 |

FOREIGN PATENT DOCUMENTS 0063640 11/1982 European Pat. Off. ............ 604/256
2055166 2/1981 United Kingdom .

OTHER PUBLICATIONS

"Wetting Tension of Polyethylene and Polypropylene Films" *American National Standard Inst.*, Designation D 2578-67 (Reapproved 1972) pp. 619-622.
"Corona-Discharge Treatment of Polyolefin Films" *Plastic Engineering*, Feb., 1977, pp. 50-52.
"Corona Surface Treaters" publication by ENI Power Systems, Inc. 4 pages.

*Primary Examiner*—Stephen C. Pellegrino
*Assistant Examiner*—Michelle Lester
*Attorney, Agent, or Firm*—Bradford R. L. Price; Paul C. Flattery; John P. Kirby, Jr.

[57] ABSTRACT

A sealing closure for a male Luer fitment includes a rigid hollow cap and flange means for a pressure lock with the fitment. The sealing closure includes a compressively retained elastomeric insert which deforms over time to compensate for creep between the fitment and the hollow cap. The sealing closure provides a liquid-tight seal over time against a pressurized liquid supply in open communication with the fitment.

13 Claims, 12 Drawing Figures

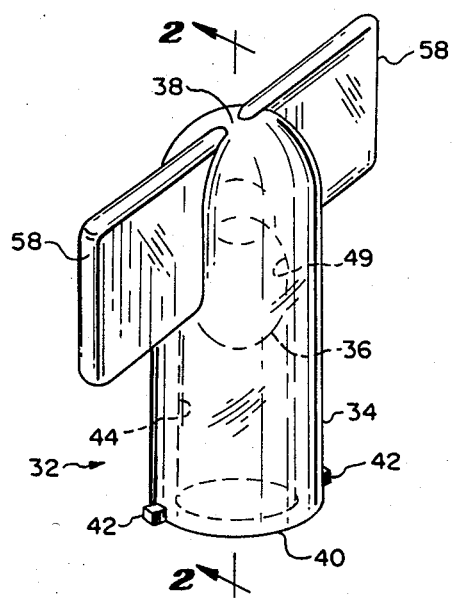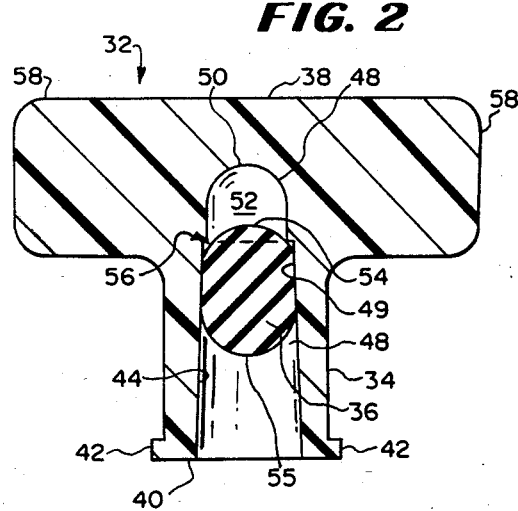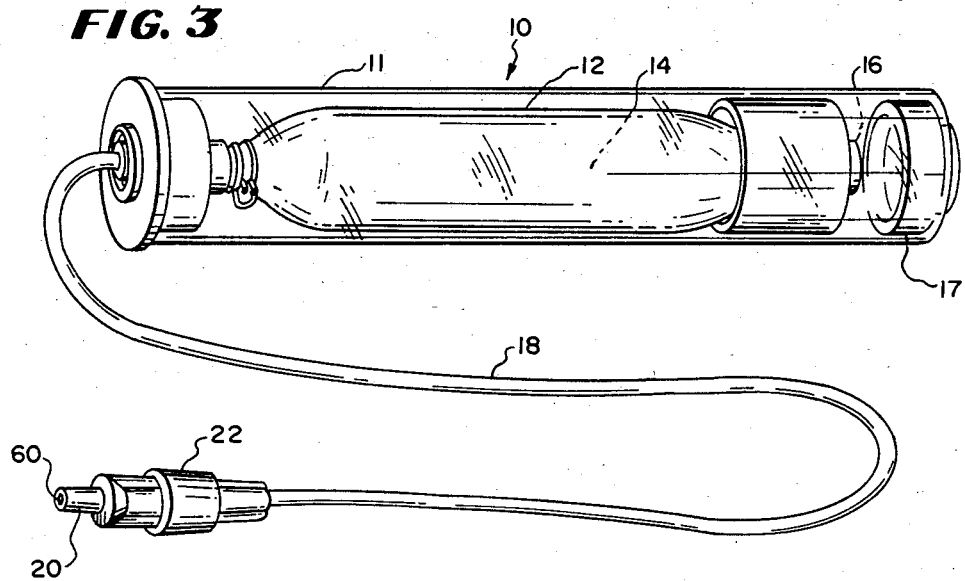

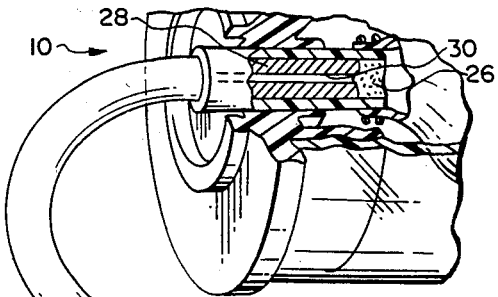
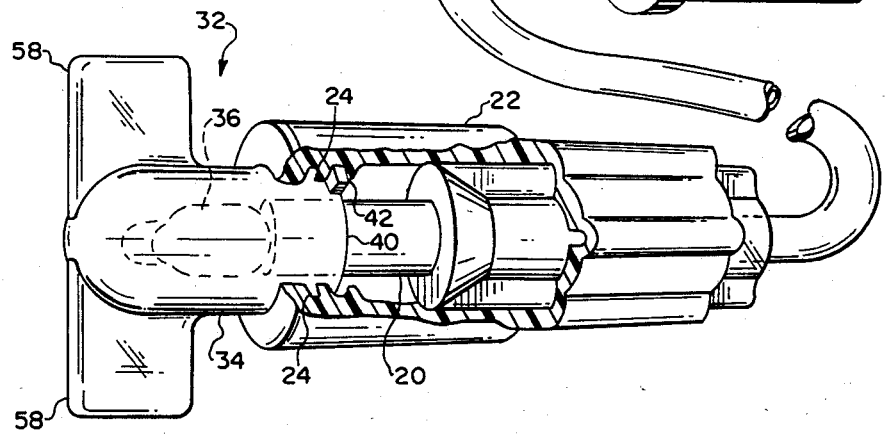
FIG. 4
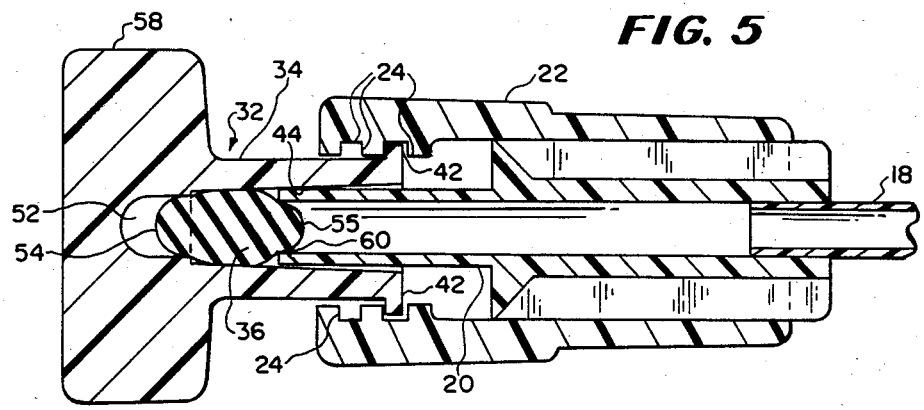
FIG. 5
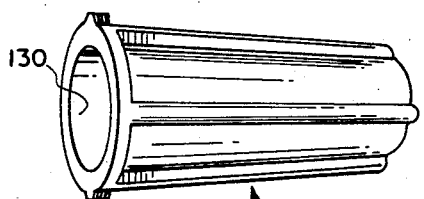
FIG. 6A
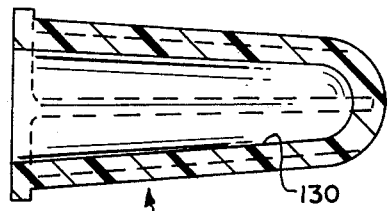
FIG. 6B
(TYPE A—PRIOR ART)

(TYPE C)

(TYPE B)

SEALING CLOSURE FOR A LUER FITTING IN OPEN COMMUNICATION WITH A PRESSURIZED LIQUID SUPPLY

TECHNICAL FIELD OF THE INVENTION

The present invention concerns a sealing closure for a Luer fitting and more particularly is directed to a closure which prevents liquid leakage from a pressurized supply reservoir that is in open communication with the Luer fitting.

BACKGROUND OF THE INVENTION

Luer fittings for Luer locks employ male and female tapered mating surfaces for a releasably secure connection between, for example, two portions of a conduit. For example, in the medical field, many intravenous fluid solution sets have at one end a tapered male Luer fitting for connection with a female Luer fitting disposed in the hub of a catheter disposed in a patient. Such male Luer fittings are used, for example, on most solution administration sets sold by Travenol Laboratories, Inc., of Deerfield, Ill.

To increase the strength of the connection between the Luer fittings, male Luer fittings often include a locking ring mounted coaxially about the male Luer fitting. The locking ring typically includes internal threads which engage flanges extending from the outside of the female Luer fitting. While the locking ring is often integral with and stationary with respect to the male Luer fitting, other locking rings are slidable relative to the fitting. An example of a Luer fitting having a locking ring which is slidable on the fitting is seen on administration set Product Code No. 2C1200, sold by Travenol Laboratories, Inc. Such a male Luer fitting having a slidable locking ring is also shown in United Kingdom Patent Application No. 8015291, Publication No. 2055166, filed May 8, 1980. A female Luer fitting is shown in that publication, as well as on the hub of a QUIK-CATH ® Catheter, Product Code No. 2N1106, sold by Travenol Laboratories, Inc.

The use of a male Luer fitting having a locking ring with a female Luer fitting having extending flanges typically does increase the security of the connection. The locking ring and flanges prevent the two Luer fittings from inadvertently separating.

The assignee of the present invention is engaged in developing disposable infusion devices for infusing quantities of medical fluid. Such an infusion device has been assigned Product Code No. 2C9056 by Travenol Laboratories, Inc., a subsidiary of the assignee of the present invention. Such a device is shown generally in U.S. Pat. No. 4,318,400 to Peery, et al. As seen in that patent, a supply of liquid to be infused into a patient is stored under pressure. Typically, such infusion devices are used by hospital pharmacists, who fill the infusors with prescribed medical fluids. The hospital pharmacist then gives the infusor to a patient who is usually ambulatory and frequently an out-patient. Thus, there is an extended period of time of, for example, up to two weeks between the time of infusor filling by the pharmacist and use by a patient.

The infusion device includes a male Luer fitting at its outlet for connection by the patient to, for example, a catheter hub. The contents of the pressurized infusor are in open communication with the male Luer fitting. Up until the development of the sealing closure of the present invention, it has been difficult to provide a female Luer-type closure for the male Luer fitting which prevents liquid leakage from the infusor reservoir. It has been found that the interlocking Luer fitments described above employing the locking ring/flange combination, while secure, are incapable of preventing liquid leakage over time from a pressurized supply. It is believed that liquid leakage occurs primarily due to cold flow or creep between the male Luer fitting on the infusor and the female Luer-type closure.

SUMMARY OF THE INVENTION

The device of the present invention provides a leak-proof sealing closure for a male Luer fitting which is an open communication with a pressurized liquid supply. The sealing closure includes a rigid, hollow cap having a closed first end and an open second end. Ridges or other flange means extend radially outwardly from the open second end of the hollow cap for engagement by the internal threads of a locking ring on the male Luer fitting that is to be sealed.

The sealing closure of the present invention includes an elastomeric insert compressibly mounted within a cavity defined by the hollow cap. While the male Luer fitting and its locking ring engage a rigid tapered surface and a rigid flange means respectively to facilitate a secure fitting, the elastomeric insert may change configuration over time to allow for creep or cold flow caused by the pressurized interfitment between the rigid surfaces of the Luer fitment and the hollow cap.

In the preferred embodiments of the invention the elastomeric insert is compressively mounted within the cavity of the sealing closure such that an end portion of the cavity remains on the closed end side of the elastomeric insert in order to provide a displacement volume for the elastomeric insert upon engagement of the sealing closure with the male Luer fitting and over time after engagement. Also, in one preferred embodiment an adhesive is provided between the elastomeric insert and the cavity wall.

DESCRIPTION OF THE DRAWINGS

FIG. 1 is a perspective view of the sealing closure according to one embodiment of the invention.

FIG. 2 is a cross-sectional view of the sealing closure of FIG. 1.

FIG. 3 is a perspective view of a liquid infusor having a pressurized liquid supply, an outlet in open communication with the liquid supply and a Luer fitting at the outlet.

FIG. 4 is an enlarged, partially cut-away, perspective view of the Luer fitting in FIG. 3, sealed by the sealing closure of the present invention.

FIG. 5 is a cross-sectional view of the sealing closure of the invention, in sealing engagement with a Luer fitting.

FIG. 6A is a perspective view of a prior art closure (Type A).

FIG. 6B is a cross-sectional view of the closure shown in FIG. 6A.

DETAILED DESCRIPTION OF THE PREFERRED EMBODIMENTS

Figure 7A:
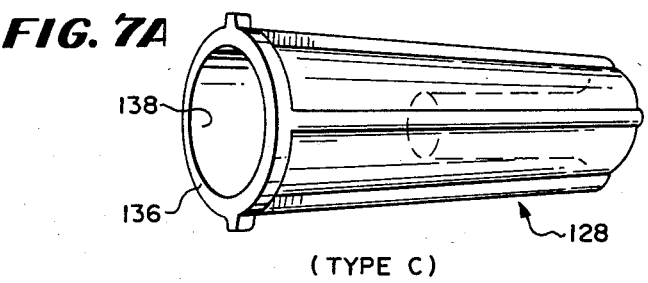
FIG. 7A is a perspective view of a modified prior art closure (Type C).

FIG. 3 illustrates an infusor 10 having a housing 11 for a unique elastomeric reservoir 12 which holds a liquid supply 14. The liquid supply 14 may be a medical fluid injected into the infusor 10 by a pharmacist or other operator. The reservoir 12 may be filled through a needle inserted through an injection site 16 in the infusor 10. A removable end cap 17 is removed to access the injection site 16. The infusor 10 is designed for accurate and constant liquid delivery from the reservoir 12 through outlet tubing 18. At the distal end of the outlet tubing 18 there is disposed a male Luer fitting 20 including a slidable locking ring 22. As seen in FIG. 4, the locking ring 22 includes internal threads 24. The interior of the outlet tubing 18 and the male Luer fitting 20 are in open communication with the reservoir 12. The infusor includes a filter 26 and a flow restrictor 28 including a capillary conduit 30, as seen in FIG. 4.

When the infusor 10 is filled with about 60 ml of liquid the stretched reservoir 12 pressurizes the liquid supply 14 in the range of about 13 PSI. If the reservoir is constructed differently, it is possible that the pressure will be higher or lower. Although the Luer fitting 20 is in open communication with the reservoir 12, the liquid supply 14 is expulsed slowly from the reservoir due primarly to the flow restrictor 28. Typical flow delivery is at a rate of about 2 ml per hour.

The infusor 10 may be filled by a hospital pharmacist according to a doctor's prescription. Since the filled infusor will perhaps not be used by a patient for as long as two weeks, the pharmacist closes the Luer fitting 20 with a sealing closure 32 of the invention. As seen in FIGS. 1 and 2, the sealing closure 32 includes a hollow cap 34 and an elastomeric insert 36. In the preferred embodiment, the hollow cap 34 is made of polycarbonate material. However, it is believed that any rigid plastic will suffice. The elastomeric insert in the preferred embodiment is a molded silicone rubber sphere.

The hollow cap includes a first end 38 and an open second end 40 opposite the first end 38. Ridges 42 or other flange means extend radially outwardly from the hollow cap 34 near the second end 40. A tapered inner surface 44 of a cavity wall defines at least a tapered portion of a cavity 48 in the hollow cap. The tapered inner surface tapers from the open second end 40 toward the cavity end 50. The cavity wall also includes a cylindrical surface 49 which defines a cylindrical portion of the cavity 48.

As seen in FIG. 2, the elastomeric insert 36 is compressively retained in the cavity by the cylindrical surface 49. In the preferred embodiment, an end portion 52 of the cavity 48 remains on the first-end side 54 of the elastomeric insert 36. A shoulder 56 projects intermediate the cavity end portion 52 and the tapered portion 46.

It is important that the elastomeric insert have a diameter larger than at least some portion of the cavity 48, so that the insert 36 can be compressively retained in the hollow cap 34. As seen best in FIG. 2, the insert 36 and cavity 48 are sized so that the insert is mounted adjacent the shoulder 56.

A pair of substantially coplanar wings 58 extend radially outwardly from the hollow cap 34 at the closed first end 38.

Operation of the sealing closure is best illustrated in FIGS. 4 and 5. The sealing closure 32 is mounted about the Luer fitting 20 with a twisting motion, thereby threading the ridges 42 into the internal threads 24 of the locking ring 22 as the tapered inner surface 44 is brought into contact with the Luer fitting 20. The wings 58 allow for easier manipulation by the operator and increase the amount of torque which may be applied to the sealing closure 32 when manipulating the sealing closure 32 into and out of engagement with the Luer fitting 20. As the sealing closure is brought into mating contact with the Luer fitting 20, the elastomeric insert 36 is compressed further. The locking ring 22 on the Luer fitting 20 and the ridges 42 on the sealing closure 32 create a pressure lock. Stated differently, the Luer fitting 20 is forcefully held in mating contact with the tapered inner surface 44. The elastomeric insert 36 creates a liquid-tight seal with the outlet 60 of the Luer fitting 20. The second-end side 55 of the insert 36 will be partially displaced into the outlet 60. Since the Luer fitting 20 and the sealing closure 32 are held under pressure, the first-end side 54 of the elastomeric insert 36 may be partially displaced into the end portion 52 of the cavity 48.

Due to the pressure lock, there is a tendency for cold flow or creep to occur in the rigid plastic material of the Luer fitting 20 and/or the hollow cap 34 of the sealing closure 32. The invention embodied by the sealing closure 32 recognizes and solves this problem by providing a relatively soft, elastomeric insert which deforms over time in response to the cold flow between the Luer fitting 20 and the sealing closure 32. The deformation of the insert prevents liquid leakage of the liquid supply 14 out of the outlet 60.

When delivery of the liquid supply 14 in the infusor 10 is desired, the patient or other operator simply unscrews the sealing closure 32 from the Luer fitting 20 by manipulating the wings 58 and throws away the sealing closure 32.

The elastomeric insert need not be molded but may instead be extruded. The insert need not be spherical in shape. For example, it is believed that an extruded cylinder having an axial opening may work as an elastomeric insert. The elastomeric insert need not be silicone rubber, but may instead be another elastomeric material such as, for example, latex rubber. In the preferred embodiment, the elastomeric insert 36 has a Shore-A hardness of about 60 durometer. However, preliminary tests indicate that a Shore-A hardness from about 40 to as high as about 70 durometer will also work.

It is believed that the sealing closure of the invention will prevent liquid leakage of the liquid supply 14 out of the reservoir 12 at pressures of 13 PSI for storage periods as long as fourteen days.

Figure 8:
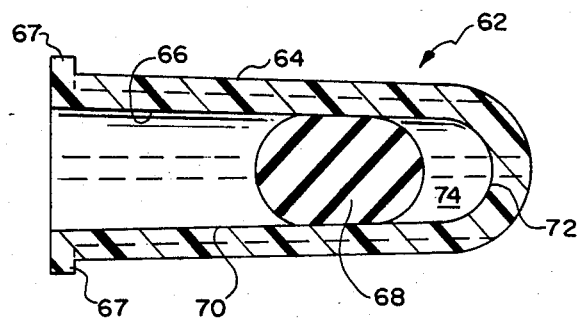
FIG. 8 is a cross-sectional view of a second embodiment of the invention (Type B).

A second embodiment of the invention is seen in FIG. 8. Here, there is no shoulder. The sealing closure 62 includes a hollow cap 64 having a tapered inner surface 66. The hollow cap 64 includes ridges 67. The elastomeric insert 68 is still compressively retained within the cavity 70. As in the first embodiment discussed above, the elastomeric insert 68 is disposed in the cavity 70 short of the cavity end 72 so that a cavity end portion 74 of the cavity 70 remains to accept gradual displacement of the elastomeric insert 68 over time.

Figure 9:
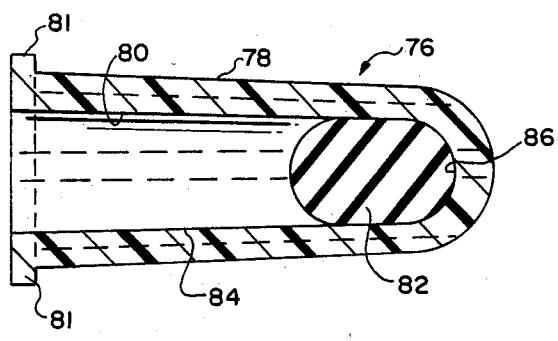
FIG. 9 is a cross-sectional view of a third embodiment of the invention.

In FIG. 9 there is illustrated a third embodiment of a sealing closure 76 of the invention, including a hollow cap 78 with a tapered inner surface 80 and ridges 81. Unlike the second embodiment seen in FIG. 8 however, here the elastomeric insert 82 and the cavity 84 are sized such that the elastomeric insert 82 is mounted adjacent the cavity end 86. It is believed that the third embodiment shown in FIG. 9 will work. It may be possible that over time the elastomeric insert 82, with no displacement volume available, will have a tendency to enable easier unlocking of the locking ring from the ridges 88 by urging against the Luer fitment and the hollow cap 78. Depending upon the required force to unlock the Luer fitment 20 from the sealing closure 76 and the strength of the seal between the insert 82 and the outlet 60, this may or may not be a desirable result.

Figure 10:
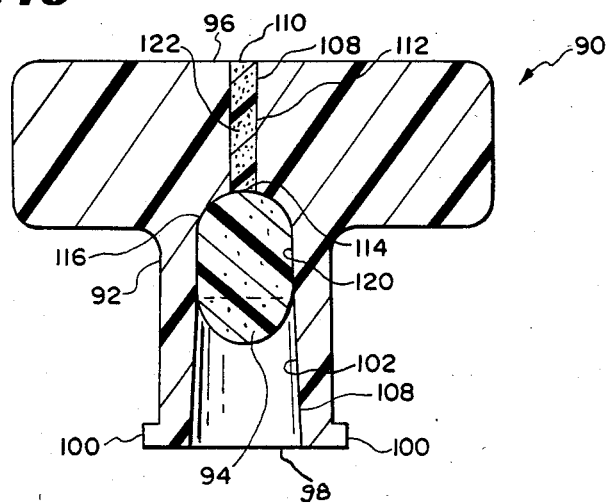
FIG. 10 is a cross-sectional view of a fourth embodiment of the invention.

A fourth embodiment of the invention is seen in FIG. 10. The sealing closure 90 seen in FIG. 10 most closely resembles the sealing closure 32 shown in FIGS. 1, 2, 4 and 5. The sealing closure 90 includes a hollow cap 92 and an elastomeric insert 94. The hollow cap 92 includes a first end 96 and an open second end 98. Ridges 100 or other flange means extend from the hollow cap 92 near the second end 98. A tapered inner surface 102 of the cavity wall defines at least a tapered portion of a cavity 108 in the hollow cap 92. The tapered inner surface 102 tapers from the open second end 98 toward the cavity end 110. In this embodiment, however, the cavity 108 extends completely through the cap 92, through the first end 96. The cavity end 110 is therefore disposed at the first end 96 of the hollow cap.

An end portion 112 of the cavity 108 remains on the first-end side 114 of the elastomeric insert 94. As with the sealing closure 32, a shoulder 116 projects intermediate the cavity end portion 112 and the cylindrical portion of the cavity 108 defined by the cylindrical surface 120.

In this fourth embodiment of the invention the sealing closure 90 further includes an adhesive 122 which seals the elastomeric insert 94 to the cavity wall. The adhesive 122 ensures that the insert 94 remains within the cap 92, even after disengagement of the sealing closure 90 from the Luer fitting 20. The adhesive 122 is preferably elastomeric in nature such that it may yield to the movement of the insert 94 which itself moves over time in response to cold flow or creep. When the sealing closure is used for a medical purpose, the adhesive should be an inert substance. Thus, the adhesive 122 is preferably a silicone such as a room temperature vulcanized silicone.

Means alternate to use of adhesive for ensuring prevention of elastomeric insert removal includes use of a matte finish on the end and inside of the Leur fitting outlet 60. The matte finish will ensure that the insert will not remain attached to the outlet 60 at the second-end side of the insert, upon removal of the Luer fitting 20. The matte finish on the Luer fitting could probably be used with all four embodiments of the sealing closure 32, 62, 76, 90.

The fourth embodiment of the sealing closure 90 is manufactured by applying a well-known corona-discharge surface treatment to the portion of the cavity wall which will encounter the adhesive 122. A corona-discharge treatment handgun made by Electro-Technic of Chicago, Ill., model BD-20 has been found to successfully apply the corona-discharge treatment. Such electrical discharge treatment prepares hard to glue surfaces such as polycarbonates for adhesion to the adhesive 122.

The cavity 108 need not extend all the way to the first end 96 but such a configuration makes easier the manufacture of the sealing closure 90 including the adhesive 122. After the corona-discharge treatment is applied, the elastomeric insert 94 is partially inserted into the cavity 108. The adhesive 122 is then injected into the cavity 108 from the cavity end 110. The insert 94 is then inserted further into the cavity until it encounters the shoulder 116. The silicone adhesive cures at room temperature and allows for displacement of the first-end side 114 of the insert 94 into the end portion 112 of the cavity 108. Under the pressurized supply storage conditions for which the sealing closure is designed, a small amount of the adhesive may be forced out the cavity end 110 over time, forming a small projection of adhesive 122 at the first end 96.

As an example only, the fourth embodiment of the invention has been constructed such that the diameter of the cavity 108 at the open second end 98 is about 0.172 inch. The diameter of the cylindrical portion is about 0.155 inch. The length of the cavity from the second end 98 to the shoulder 116 is about 0.360 inch, with the length of the tapered portion being about 0.250 inch. The diameter of the end portion 112 is about 0.100 inch. The diameter of the spherical elastomeric insert 94 is about 0.175 inch.

The first and fourth embodiments of the invention are preferred. The first embodiment is less expensive than the fourth embodiment but the fourth embodiment is less likely to allow removal of the elastomeric insert. Removal of the insert is not a problem because the sealing closure should not be re-used, to avoid contamination, and also because the insert can be easily removed from the Luer fitting by the patient. However, removal of the insert may be perceived as a disadvantage, making it less acceptable commercially.

Figure 7B:
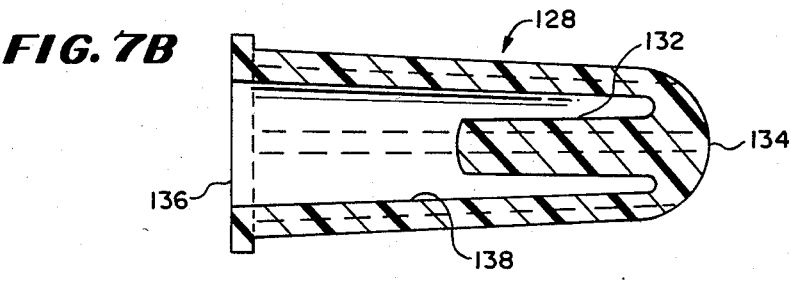
FIG. 7B is a cross-sectional view of the closure shown in FIG. 7A.

A small comparison test utilizing one of the sealing closures of the invention has been performed. The sealing closure 62 shown in FIG. 8 and referred to as Type B in the test was compared with the closures 126, 128 illustrated in FIGS. 6 and 7, respectively, and referred to in the test as Types A and C, respectively. The Type A closure 126 is a prior art closure having a tapered inner surface 130. The Type C closure 128 shown in FIG. 7 is a modified closure including a rigid upstanding column 132 extending from the closed end 134 toward the open end 136. The Type C closure 128 also includes a tapered inner surface 138.

Thirty samples of the Type A closure 126, thirty samples of the sealing closure 62 (Type B) of the present invention and twenty-one samples of the Type C closure 128 were tested. The test was performed by attaching each of the closures to a filled infusor 10 and storing at room temperature for three days. After this storage period the infusors 10 with attached closures were inspected. Nineteen leaks occurred at the Type A closures 126 and eighteen leaks occurred at the Type C closures 128. There were no leaks at the Type B sealing closure 62 of the invention.

While several embodiments and features of the invention have been described in detail herein and shown in the accompanying drawings, it will be evident that various further modifications are possible without departing from the scope of the invention.

What is claimed is:

1. A removable sealing closure for a male Luer fitting that is in open communication with a pressurized liquid supply, the male Luer fitting being of the type including a locking ring, the sealing closure comprising:
   (a) a rigid, hollow cap including
      (i) a first end, (ii) an open second end opposite said first end, (iii) flange means extending radially outwardly from said hollow cap, near said second end, for engagement by the locking ring and (iv) a tapered inner surface forming at least a tapered portion of a cavity wall in said hollow cap, said tapered inner surface tapering inwardly from said open second end at the beginning of a cavity defined by said cavity wall, for interfitment with a male Luer fitting;

(b) an elastomeric insert compressively retained by said hollow cap in said cavity, short of the end of said cavity such that at least an end portion of said cavity remains on the first-end side of said elastomeric insert; and (c) an elastomeric adhesive in said cavity end portion between said elastomeric insert and said cavity wall;

(d) such that said removable sealing closure is adapted to create a liquid-tight seal between said elastomeric insert and an outlet of the male Luer fitting and wherein said elastomeric insert is partially displaced into the outlet of the male Luer fitting upon mating contact of the Luer fitting and said tapered inner surface and securement of the locking ring to said flange means.

2. The sealing closure as in claim 1, further including a shoulder intermediate said cavity end portion and said tapered portion, said shoulder serving as a stop to said elastomeric insert, even upon interfitment of said sealing closure with the male Luer fitting, and allowing for partial displacement of said elastomeric insert into said cavity end portion.

3. The sealing closure as in claim 2, said cavity further including a cylindrical surface defining a cylindrical portion of said cavity, said cylindrical portion disposed intermediate said shoulder and said tapered portion, wherein said cylindrical portion has a diameter not greater than about 0.155 in. and said elastomeric insert has a diameter of at least about 0.175 in.

4. The sealing closure as in claim 1, wherein said sealing closure prevents liquid leakage from the male Luer fitting when a male Luer fitting is in open communication with a liquid supply stored at a pressure of up to about 13 PSI for storage periods of up to fourteen days.

5. The sealing closure as in claim 1, wherein said elastomeric insert is silicone rubber.

6. The sealing closure as in claim 1, further including a pair of substantially coplanar wings extending radially outwardly from said hollow cap at said first end to facilitate manipulation of said sealing closure into and out ot engagement with a male Luer fitting.

7. The sealing closure as in claim 1, wherein said adhesive comprises room temperature vulcanized silicone.

8. The sealing closure as in claim 1, wherein said elastomeric insert is a sphere.

9. The removable sealing closure as in claim 1, wherein said cavity extends through said first end.

10. A sealing closure and male Luer fitting combination comprising:

(a) a pressurized liquid supply;

(b) a male Luer fitting disposed in open liquid communication with said liquid supply, said male Luer fitting including a locking ring thereabout and an outlet; and (c) said sealing closure being removable from said male Luer fitting and including a rigid, hollow cap having (i) a first end, (ii) an open second end opposite said first end, (iii) flange means extending radially outwardly from said hollow cap, near said second end, for engagement by the locking ring, (iv) a tapered inner surface forming at least a tapered portion of a cavity wall in said hollow cap, said tapered inner surface tapering inwardly from said open second end at the beginning of a cavity defined by said cavity wall, for interfitment with said male Luer fitting, (v) an elastomeric insert compressively retained by said hollow cap in said cavity, short of the end of said cavity such that at least an end portion of said cavity remains on the first-end side of said elastomeric insert, and (vi) an elastomeric adhesive in said cavity end portion between said elstomeric insert and said cavity wall.

11. The sealing closure and male Luer fitting combination as in claim 10, wherein said elastomeric insert is partially displaced into the outlet of said male Luer fitting when said sealing closure is mounted thereabout.

12. The sealing closure and male Luer fitting combination as in claim 11, wherein said elastomeric insert is a sphere.

13. The removable sealing closure and male Luer fitting combination as in claim 10, wherein said cavity extends through said first end.

* * * * *